United States Patent [19]

Machida et al.

[11] Patent Number: 5,019,386
[45] Date of Patent: May 28, 1991

[54] HEPATITIS B VACCINE

[75] Inventors: Atsuhiko Machida, Kanagawa; Tetsuo Nakamura, Tokyo, both of Japan

[73] Assignee: Institute of Immunology Co., Ltd., Koraku, Japan

[21] Appl. No.: 239,028

[22] Filed: Aug. 29, 1988

Related U.S. Application Data

[63] Continuation of Ser. No. 759,207, Jul. 26, 1985, abandoned.

[30] Foreign Application Priority Data

Jul. 31, 1984 [JP] Japan .................................. 159124/84

[51] Int. Cl.$^5$ ......................... A61K 39/29; C07K 7/08
[52] U.S. Cl. ....................................... 424/89; 424/88; 424/85.8; 530/326; 530/300; 514/2; 514/13
[58] Field of Search ..................... 424/88, 89; 530/326, 530/300; 514/2, 13

[56] References Cited

U.S. PATENT DOCUMENTS

| 4,415,491 | 11/1983 | Vyas ...................................... 424/89 |
| 4,554,101 | 11/1985 | Happ ........................................ 514/2 |
| 4,563,423 | 1/1986 | Murray et al. ......................... 435/68 |
| 4,596,792 | 6/1986 | Vyas ...................................... 424/89 |
| 4,599,230 | 7/1986 | Milich et al. ............................ 424/88 |
| 4,599,231 | 7/1986 | Milich et al. ............................ 424/88 |
| 4,666,713 | 5/1987 | Skelly et al. ........................... 424/89 |
| 4,683,136 | 7/1987 | Milich et al. ............................ 424/89 |
| 4,778,784 | 10/1988 | Dreesman et al. .................. 530/326 |
| 4,816,564 | 3/1989 | Ellis et al. ............................. 530/324 |
| 4,818,527 | 4/1989 | Thornton et al. ..................... 424/89 |
| 4,847,080 | 7/1989 | Neurath et al. ....................... 424/86 |

FOREIGN PATENT DOCUMENTS

| 0174444 | 3/1986 | European Pat. Off. ............... 424/88 |
| 2550203 | 2/1985 | France .................................. 424/88 |

OTHER PUBLICATIONS

Michel et al. (Abst.) #8A.16, 1984 Inter. Sym. on Viral Hepatitis, 3/8–10/84.
Michel et al., *PNAS*, 81, 1984, pp. 7708–7712.
Machida et al., *Gastroenterology*, 85, 1983, pp. 268–274.
Machida et al., *Gastroenterology 86, 1984, pp. 910–918*.
Neuwrath et al., *Science*, 224, 1984, pp. 392–395.
Thung et al., *Liner.* 1, 1981, pp. 75–80.
Happ et al., *PNAS*, 78(6), 1981, pp. 3824–3828.
CA #86252n, vol. 99, 1983 Machida et al.

*Primary Examiner*—Garnette D. Draper
*Attorney, Agent, or Firm*—Beveridge, DeGrandi & Weilacher

[57] ABSTRACT

A polypetide vaccine is disclosed with the amino acid sequence of Asp-Pro-Arg-Val-Arg-Gly-Leu-Try-Phe-Pro-Ala-Gly-Gly-Ser-Ser-Ser-Gly-Thr-Val that bears the receptor for polymerized human serum albumin capable of raising antibodies to inhibit the access and entry of hepatitis B virus (HBV) to hepatocytes. The polypeptide vaccine is also shown in FIG. 1 SCHEME OF POLYEPTIDES (P22,P27) AND POLYEPTIDES (P31,P35) POSSESSING BINDING SITE WITH POLY-HSA.
(oo : AMINO ACID RESIDUE)

HEPATITIS B VACCINE

The present invention relates to hepatitis B vaccine.

On a world-wide scale, the infection with hepatitis B virus (HBV) represents one of the major problems in public health care. There are an estimated 200 million persons who are carriers of HBV. These carriers are mostly asymptomatic, that is, they exhibit little or no symptoms of the disease. However, some of these persons develop a spectrum of hepatic diseases ranging from acute hepatitis to hepatocellular carcinoma. Furthermore, they constitute a reservoir of HBV in the community from which the virus is transmitted vertically (perinatal infection from mother to child) and horizontally (through intimate body contacts).

A viral infection of a healthy organism occurs when a virus attaches itself to a receptor site on the cell, enters the cell and then takes over the cell's machinery to make copies of the virus. Eventually the cell lyses or bursts. Antibodies function by attaching themselves to the virus and blocking its ability to attach to the host cells.

The technology of vaccines and vaccination must surely rank as one of the most important developments of all times. Some diseases have been virtually eliminated thereby while others have been brought under control with a considerable savings in human lives. In general, the process of vaccination is carried out by injecting a virus into a living host in order to make antibodies capable of neutralizing or inhibiting the virus. The virus that is used for this injection process is normally a killed virus or an attenuated virus; that is, a virus that has been reduced in virulence by passage through a animal host. However successful these procedures have been, they are not without problems. For example, an attenuated virus can mutate and increase in virulence; also the long term effect of such latent viruses is not fully known. Still further, killed viruses may not be completely inactivated and may cause infections.

Other problems also arise because of the fact that the virus must be grown in order to produce killed virus or attenuated virus vaccines. Therefore, there is a potential for accidental venting of such organisms to the environment. Thus, there is the need for special handling and storage vacilites for such substances which need may become difficult to fulfill in some underdeveloped countries.

As a result of the problems that have been encountered over the years in producing, storing and using vaccines produced from viruses, efforts have been made to produce synthetic vaccines. These synthetic vaccines are not based on killed viruses or attenuated viruses but consist of short protein chains called "peptides". The concept of the peptides or synthetic vaccines is to synthesize in the laboratory a short protein chain that mimics a small region of the outer coat of the virus and which is capable of stimulating the production of antibodies in the host that will neutralize the virus and prevent the virus from infecting a cell. The synthetic peptide, like the virus itself, elicits the production of antibodies by the host while antibodies will then function to bind to the surface of the virus and neutralize the virus by blocking the sites whereby the virus would be able to attach to healthy cells to initiate the infection process.

HBV has been shown by research workers to be a unique DNA virus with a diameter of 42 nm made of an internal core representing viral nucleocapsid and an outer coat. These constituents of HBV are different antigenically. Outer coat is made of viral protein with the antigenicity of hepatitis B surface antigen (HBsAg), whereas inner core or core particles contain nucleoprotein with a molecular size of 19,000 daltons (P19), in addition to the viral DNA and its polymerase. P19 bears the antigenicity of both hepatitis B core antigen (HBcAg) and hepatitis B e antigen (HBeAg). HBeAg is expressed along the N-terminus, while HBcAg is expressed at the part exposed to the surface when P19 molecules are assembled to make the core particle. In hepatocyte infected with HBV, the viral coat, HBsAg, is produced far in excess of core particles, so that HBsAg itself appears in the circulation in spherical and tubular forms both with a diameter of 22 nm. DNA viruses that closely mimic HBV are found in species other than humans, such as woodchuck, duck and ground squirrel, and constitutes a family that is called hepadna virus.

The fact that viral nucleocapsid is covered with HBsAg can be taken advantage of for the prevention of HBV infection by immunological means. Antibody to HBsAg (anti-HBs) is given to suceptible persons for a passive immunoprophylaxis, and 22-nm HBsAg particles are used as a vaccine for an active immunoprophylaxis.

It is widely known that HBV has a narrow host range and narrow organ spcificity. Tests have established that only hepatocytes from humans and chimpanzees are vulnerable to HBV infection. Such organ tropism would be responsible for the site on HBV that gains access to human and chimpanzee hepatocytes with a specifity of "lock and key."

The Receptor for Polymerized Human Serum Albumin

Factors that react with polymerized human serum albumin (poly-HSA) have been identified in serums from patients with various hepatic disorders and ascribed to antibodies against denatured albumin molecules. For reasons not fully understood, these factors detected by the agglutination of sheep red blood cells (SRBC) coated with poly-HSA, were found preferentially more often in serums positive for HBeAg.

HBV infection can be divided into the HBeAgphase when HBeAg can be detected in the serum along with Dane particles (presently accepted HBV) and the anti-HBe phase when antibody to HBeAg is detected but Dane particles are detected only rarely. It has been found that not every HBsAg-positive serum agglutinates SRBC coated with poly-HSA; HBsAg-positive serums containing HBeAg show much higher agglutination titer than those containing anti-HBe. Unexpectedly, the agglutination of poly-HSA-coated cells by HBsAg-positive serums is not due to antibodies as was initially suspected.

Applicants have found that Dane particles, as well as HBsAg particles are directly involved in the reaction with poly-HSA-coated cells. Utilizing immune electron microscopy, Dane particles and 22-nm HBsAg particles derived from HBeAg-positive plasma were shown to aggregate in the presence of poly-HSA, in contrast to 22-nm HBsAg particles obtained from anti-HBe-positive plasma that did not show such aggregation. On the basis of these observations, a receptor for poly-HSA has been described by applicants on the surface of Dane particles and 22-nm HBsAg particles that co-occur with HBeAg, but not on 22-nm particles that co-exist with anti-HBe.

The poly-HSA receptor of HBAg was species-specific, because it will react with polymerized albumins from human and chimpanzee, but will not react with polymerized albumins from animals without a susceptibility to HBV, such as mouse, rabbit and horse. These observations by applicants strongly suggested that the poly-HSA receptor on HBV would be involved in the species specificity of the virus in infecting hepatocytes.

Albumin is produced in hepatocytes and represents the most abundant protein in the circulatory system. A constant level of albumin is maintained in the bloodstream. Aged albumin molecules aggregate spontaneously and are taken up and away by hepatocytes that have the receptor for aggregated (polymerized) albumin. Human and animal hepatocytes are known to have the receptor for polymerized albumin, but not for a monomeric albumin of their own and other species. Aggregated albumin molecules forming constantly in the circulation, therefore, adhere to hepatocytes by means of their receptor for poly-HSA. When Dane particles are introduced into the circulation, they would be able to gain entry to hepatocytes by way of the poly-HSA that acts as a connector. As such, the affinity of HBV to hepatocytes would be not a direct one. It would be ascribable to the mutual affinity to a third party which can bridge them and operate for their coming in contact.

HBsAg With The Receptor For Poly-HSA

HBsAg particles derived from HBeAg-positive plasma and bearing the receptor for poly-HSA banded at a higher density (1.213 g/cm$^3$) than those obtained from anti-HBe-positive plasma and without the receptor (1.203 g/cm$^3$), in a rate zonal ultracentrifugation in CsCl. When the heavy HBsAg particles were treated with pronase, their density was lowered to approach to that of light HBsAg particles along with the loss of the receptor reactivity. These observations indicated that HBsAg particles that co-occur with the receptor are associated with additional molecules that are responsible for the receptor.

When HBsAg particles derived from HBeAg-positive plasma were broken into constituent polypeptides by a treatment with detergent and reducing agent, polypeptides with estimated molecular size of 31,000 and 35,000 daltons were revealed, in addition to the major polypeptide of HBsAg composed of 226 amino acid residues (P22) and its glucosylated form, P27. HBsAg particles from HBeAg-positive plasma were much richer in the content of P31 and P35 than those derived from anti-HBe-positive plasma (11.4±0.3% vs. 1.6±0.4% on the basis of their percentage in the densitometer tracing, $P<0.001$). P35 had the same amino acid composition as that of P31, and the difference in their molecular size was attributed to a carbohydrate moiety attached to P35, just like in the relation of P27 to P22. Both P31 and P35 exhibited the binding activity to poly-HSA with a binding curve quite similar to that of HBsAg particles with the receptor. On the basis of these findings, P31 (and P35) was considered to be responsible for the poly-HSA receptor on the HBsAg particles derived for HBeAg-positive plasma. The fact that P31 was capable of binding with polymerized albumins from humans and chimpanzees, but not to those from animals without susceptibility to HBV, was additional evidence in support of such view.

Using polypeptide composition and terminus amino acid sequence as a guide, amino acid sequence of P31 was searched for on the nucleotide sequence of HBV-DNA of the same subtype (adr) as HBsAg particles that served a source of P31. P31 had the C-terminus amino acid sequence of -Val-Tyr-Ile, identical to that of P22. Adjacent to the N-terminus of P22, there is a region called "pre-S". On the sequence of pre-S region, the 55th amino acid residue from the N-terminus of P22 was reported to be methionine, irrespective of subtypes. The putative amino acid sequence of 281 residues (226 for P22 plus the adjacent 55 in the pre-S region creating a molecular size of 31,142 daltons) was calculated to have the amino acid composition very similar to that determined for P31.

Since P22 did not exhibit the receptor reactivity, the amino acid sequence of 55 residues on P35 that is encoded by the pre-S region of HBV-DNA was reasonably suspected to bear the receptor. Because there were no methionine residues between the N-terminus of P22 and 55th amino acid counted into the pre-S region from it, a method capable of splitting polypeptide at methionine residues, such as CNBr was expected to liberate the pre-S amino acid sequence from P35.

When P31 was treated with CNBr and then subjected to high-performance liquid chromatography, a peptide with estimated molecular size of 8,000 daltons (P8) was obtained. P8, associated with a carbohydrate moiety, had an amino acid composition almost identical to that of the 55-amino acid polypeptide in the pre-S sequence. Furthermore, P8 was found to be capable of binding with polymerized albumins only from humans and chimpanzees, thereby indicating that it bears the receptor for poly-HSA.

Synthetic pre-S Peptides And HBsAg Polypeptides With The Receptor For Poly-HSA As Novel Hepatitis B Vaccines Along the amino acid sequence of the pre-S region of HBV-DNA's of 3 different subtypes, a region of high local hydrophilicity was identified by applicants. A peptide of 19 amino acid residues containing the region with the high local hydrophilicity and commonly expressed by HBV-DNA's of subtypes adr and ayw, was chemically synthesized (the sequence of HBV-DNA of subtype adw wad different only in that it had leucine as the 9th amino acid residue in place of phenylalanine of HBV-DNA's of the other subtypes). The peptide was designated Asp-peptide by applicants and when conjugated with ovalbumin and emulsified in Freund's complete adjuvant, could raise antibodies in guinea pigs that bound with HBsAg with the receptor.

Applicants' findings therefore indicated that the Asp-peptide, as well as P31 and P35 bearing the receptor for poly-HSA, may be used as hepatitis B vaccines. They are different in principle from conventional vaccines in a form of HBsAg particles, in that they can raise antibodies that specifically block the site on HBV (poly-HSA receptor) that is required for its gaining access and entry to hepatocytes.

The availability of Asp-peptide is limited only by the constraints of chemical synthesis. Moreover, it may well raise protective antibodies in non-responders to the conventional HBsAg vaccine also who are estimated as 5% of all vaccines.

SUMMARY OF THE INVENTION

HBV is transmitted by blood and its products contaminated with the virus. HBV was discovered by Dane and his co-workers in 1970 in blood containing Australia antigen (hepatitis B surface antigen, HBsAg), and represents a spherical DNA virus with an internal core. Plasma of humans infected with HBV, when ultracentrifuged and observed in an electron microscope, reveals large spherical particles with a diameter of 42 nm (Dane particles) and small spherical and tubular particles with a diameter of 22 nm.

The Dane particle has an internal core with a diameter of 27 nm (core particle) that is covered with an outer shell. The core of Dane particles contains a circular, double-stranded DNA with an estimated molecular size of $1.6 \times 10^6$ daltons and a DNA polymerase.

The outer coat of Dane particle bears the antigenicity of HBsAg. The surface of the internal core expresses a distinct antigenicity called hepatitis B core antigen (HBcAg). In the core particle, the unit nuclear polypeptides with an approximate molecular size of 19,000 daltons (P19) are contained. A part of P19 is exposed on the surface of core particles and expresses the antigenicity of HBcAg. Another part of P19 toward its N-terminus bears the antigenicity of hepatitis B e antigen (HBeAg) and may appear in the circulation.

Overall, therefore, there are 3 HBV-associated antigens presently identified, i.e., HBcAg, HBsAg and HBeAg. HBsAg bears the determinant a that is commonly expressed by HBV's of different strains. In addition, it bears subtype-specific antigenic determinants. From the difference in the antigenicity, 4 subtypes of HBsAg are presently recognized, i.e., adr, adw, and ayr. These subtypic antigenicities are attributed to minor differences in amino acid sequences of HBsAg coded for by HBV's of different strains.

HBV is transmitted by the transfusion of blood units from HBV carriers, and also through needle and razor blades contaminated with HBV. For example, in Japan the annual incidence of fulminant hepatitis is estimated at 4,400 cases and that of acute hepatitis 180,000 cases. HBV infection is implicated in about 30% each of 300,000 patients with chronic hepatitis and 120,000 with liver cirrhosis. Moreover, about one half of 8,400 cases of primary hepatocellular carcinoma is suspected of an etiology related to HBV infection.

Besides such populations with overt clinical disease, there are estimated 200 million asymptomatic carriers, including 3 million in Japan. Among advanced countries, the rate of HBV carriers to the total inhabitants is the highest in Japan. People in Japan, therefore, are at high risk of contracting HBV infection. Since the problem is a world-wide problem there exist a need for the development of efficient and safe synthetic vaccines for the prevention of HBV infection.

Hepatitis B vaccines in present use are 22-nm spherical HBsAg particles purified from antigen-positive plasma and then inactivated. Limited availability of human plasma as a source of vaccine, taken together with the failure of cultivating HBV in vitro, is one of the reasons for a high price of vaccine. In addition, proteins other than HBsAg, or even unidentified viruses, might co-purify in the process of preparing HBsAg from plasma. Other problems utilizing virus to make vaccines have been mentioned above. Therefore, efforts have been made to develop synthetic vaccines. The present invention is timely in meeting with such demands, because it provides (poly)peptide vaccines that are safe and efficacious in preventing HBV infection.

DETAILED DESCRIPTION OF INVENTION

The present invention is based on the novel findings of applications in regard to the attachment of HBV to hepatocytes. See the published works by applicant and their laboratory assistants in *Gastroenterology* 1983, 85:268-74 and 1984; 86:910-9 the entire disclosures of which are relied on and incorporated herein. Applicants have determined that HBV gains access to hepatocytes by means of the receptor of polymerized human serum albumin (poly-HSA) in a species- and organ-specific manner, and that the amino acid sequence bearing the receptor for poly-HSA is located on HBsAg.

Applicants have identified the poly-HSA receptor on a HBsAg polypeptide, P31, that can be purified from HBsAg particles derived from HBeAg-positive plasma. The major polypeptide of HBsAg, P22, did not adhere to poly-HSA, and therefore, was devoid of the receptor.

Figure 1:
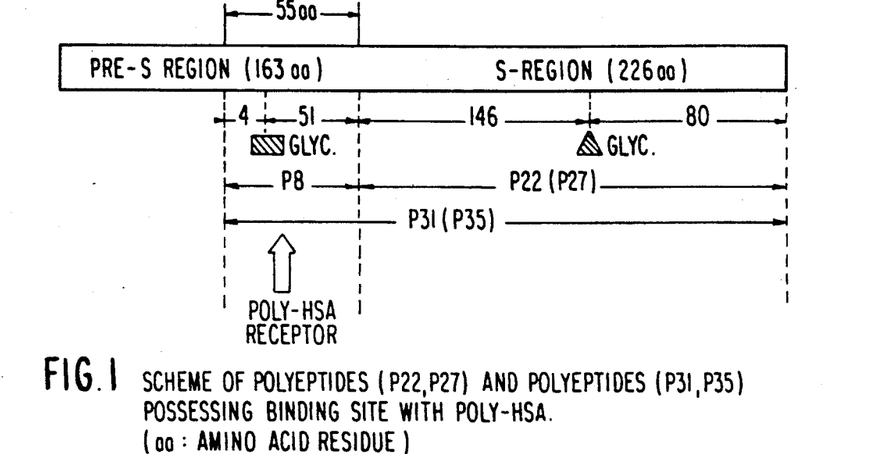
FIG. 1 shows a schematic representation of polypeptide sequences and polypeptide processing binding sites with poly-HSA.

Further attempts to correlate P31 with the nucleotide sequence of HBV-DNA permitted applicants to determine that the protein portion of P31 is composed of P22 made of 226 amino acid residues coded by the S region of HBV-DNA plus the 55 amino acid residues coded by the pre-S region in the upstream of the S region. This is shown in FIG. 1.

Accordingly, the poly-HSA receptor was reasonably presumed to be present on the pre-S amino acid sequence composed of 55 residues. In support of this view, the 55-amino acid pre-S polypeptide was released by splitting P31 with CNBr, and found to bear the poly-HSA receptor.

The polypeptide vaccine, P31, represents a hepatitis B vaccine capable of raising antibodies that specifically block the poly-HSA receptor on HBV that is required for its attachment with human hepatocytes.

The capability of P31 polypeptide as a hepatitis B vaccine can be fully accomplished by P35, that is P31 glucosylated as Asn located at the 4th amino acid residue from the N-terminus located in the sequence coded by the pre-S-region of HBV-DNA.

The polypeptide vaccine, P31, may be produced by the method as follows.

Plasma from any suitable source such as human containing a high reversed passive hemagglutination titer of HBsAg and positive for HBeAg is centrifuged to spin down Dane particles. Any suitable centrifuge device for biological process may be used. The supernatant is subjected to continuous-flow zonal ultracentrifugation followed by rate zonal ultracentrifugation in KBr and sucrose, and small spherical HBsAg particles with a diameter of 22-nm are obtained.

Purified 22-nm HBsAg particles are broken into constituent polypeptides by incubation at 37° C. for 30 min in Tris-HCl buffer (0.01M, pH 8.0) containing 1%

(vol/vol) SDS and 1% (vol/vol) 2-mercaptoethanol. HBsAg polypeptides thus obtained are factionated by polyacrylamide gel electrophoresis after the method of Maizel. Fractions containing P31 are subjected to gel filtration in a column of Sephadex G-25 (Pharmacia Fine Chemicals, Piscataway, N.J.) equilibrated with water, and void volume fractions containing P31, but without reagents for electrophoresis such as SDS, are collected and lyophlized.

Physicochemical Properties of P31

Amino Acid Analysis: 10 μg of P31 was hydrolysed with constant-boiling 6N HCl in an evacuated, sealed tube of 110° C. for 24, 48 and 72 hours, and then subjected to a Hitachi 835 amino acid analyser (Hitachi Ltd., Tokyo, Japan). The highest values at different incubation periods were adopted for leucine, isoleucine and valine. The values for threonine and serine were extraported as time zero.

(a) Amino Acid Composition (expressed at the nearest moles per mole):

| | |
|---|---|
| aspartic acid | 5 |
| asparagine | 9 |
| threonine | 24 |
| serine | 31 |
| glutamic acid | 2 |
| glutamine | 8 |
| glycine | 18 |
| alanine | 9 |
| valine | 14 |
| methionine | 7 |
| isoleucine | 16 |
| leucine | 38 |
| tyrosine | 6 |
| phenylalanine | 20 |
| lysine | 2 |
| histidine | 2 |
| arginine | 10 |
| proline | 32 |
| tryptophane | 14 |
| cysteine | 14 |

(b) Terminus Amino Acid Residue: The N-terminus amino acid was determined by the manual Edman degradation. P31 was digested with carboxypeptides A (Worthington Biochemical Corp., Freehold, N.J.) in the presence of ethylmorpholine-HCl (0.2M, pH 8.5) at 25° C. for 15 min, and then subjected to amino acid analysis for the determination of C-terminus amino acid sequence. The N-terminus amino acid was methionine, and the C-terminus amino acid sequence was -Val-Tyr-Ile.

Molecular Size: 31,000 daltons based on the migration in SDS polyacrylamide gel electrophoresis Heat Stability: Stable after 20 min at 100° C.

Absorbance: lambda max at 280 nm with a shoulder at 290 nm

To further determine the precise amino acid sequence on P31 that is capable of binding with poly-HSA, the following was carried out: Along the nucleotide sequence on HBV-DNA's of 3 different subtypes coding for 55-amino acid pre-S polypeptide, a sequence of 19 amino acid residues was selected that displayed a high local hydrophilicity and expressed in common by HBV of 3 different subtypes. The peptide synthesized chemically and named Asp-peptide has the following sequence: Asp-Pro-Arg-Val-Agr-Gly-Leu-Try-Phe(or-Leu)-Pro-Ala-Gly-Gly-Ser-Ser-Ser-Gly-Thr-Val. HBsAg particles without the receptor for poly-HSA, when cojugated with Asp-peptide, acquired the binding activity with poly-HSA by way of this peptide. Data in Table 1 shows the Asp-peptide reacted very well as shown by the high number of counts measured by radioactive labelling. Furthermore, Asp-pepteide has now been found by applicant to express the immunogenicity, and therefore, can be used as a hepatitis B vaccine. Asp-peptide vaccine is therefore an important feature of the invention. The antibody raised against Asp-peptide in guinea pigs bound to HBsAg particles derived from HBeAg-positive plasma, but barely with those obtained from anti-HBE-positive plasma. Based on these observations, antibodies directed to Asp-peptide can block the receptor on HBV and prevent it efficaciously from gaining access to hepatocytes by way of poly-HSA present on their surface.

TABLE 1

Reaction of Asp-peptide-HBs, HBsAg(PAreceptor ⊕)P31 and Polymerized Albumin
Method: Sandwich method which utilize polymerized albumin as solid phase, anti-HBs antibody(horse) as labelling 2nd antibody.

≢—polymerized-sample-$^{125}$I-anti-HBs(Horse)
albumin

| | a | b | c | d | e |
|---|---|---|---|---|---|
| Human | 5524 | 166 | 28370 | 4587 | 181 |
| Control | 1767 | 258 | 358 | 192 | 168 |
| | | | | | (cpm) | a: Asp peptide-HBs
b: HBsAg (PAreceptor ⊖) #80
c: HBsAg (PAreceptor ⊕) #122
d: P31
e: negative control Monoclonal antibodies were raised against Asp-peptide and P31, as well as against HBsAg particles treated with SDS and 2-mercaptoethanol and split into constituent polypeptides. All monoclonals that bound to Asp-peptide could block the binding of poly-HSA with HBsAg bearing the receptor. This is shown in Table 2. These results stand in further support to the view that Asp-peptide represents a synthetic vaccine with a remarkably high efficacy.

TABLE 2

Characterization of anti-Pre-S monoclonal antibody.
Method: Asp; Sandwich method which utilize Asp polypeptide as a solid phase anti-mouse serum as a labelling 2nd antibody.

≢—Asp-polypeptide-Sample-$^{125}$I-anti-mouse

P.A. inhibition; Inhibition method which utilize P-HSA(or P-CSA) as a solid phase, anti-HBs antibody as a labelling 2nd antibody, and mix the sample with HBsAg having PAreceptor.

≢— P-HSA or P-CSA ⟨ HBs(P.A. +)-$^{125}$I-anti-HBs Sample

| Monoclonal antibody (1) | | P.A. inhibition | |
|---|---|---|---|
| Hyb # | Asp- | Human | Chimpanzee |
| 5501 | 9094 | 482 | 231 |
| 05 | 7664 | 370 | 229 |
| 10 | 8425 | 182 | 221 |
| 14 | 8548 | 154 | 212 |
| 17 | 9352 | 190 | 203 |
| 20 | 11172 | 34 | 245 |
| 35 | 7687 | 121 | 180 |
| 36-A | 7873 | 161 | 210 |
| Control | 60 | 8382 | 11307 |

TABLE 2-continued

| | (cpm) |
|---|---|

(1) Monoclonal antibody obtained by immunization of Asp peptide.

It has been mentioned that the 9th amino acid residue of phenylalanine in the Asp-peptide may be placed by leucine. This is attributable to a slight variation occurring in the pre-S amino acid sequences among HBV of different subtypes. On the sequence of 19 amino acid residues of Asp-peptide, the 9th residue is phenylalanine for HBV-DNA's of subtypes adr and ayw, but it is leucine for the HBV-DNA of subtype adw; all the remaining sequence is shared by HBV of 3 different subtypes.

Despite this difference, the antibodies raised against Asp-peptide with the 9th residue of phenylalanine did not show any preference for subtypes in the binding with the pre-S polypeptide; they bound also with HBsAg particles of subtype ayw derived from HBeAg-positive plasma.

The Asp-peptide was synthesized by the solid-phase method of Merrified et al. (Adv. Enzymol. 32:221–296, 1969). This entire publication is relied on and incorporated herein by reference. The synthesized peptide was hydrolysed under a depressurized condition with 6N HCl at 110° C. for 24 hours, and the obtained amino acid composition was confirmed to be identical with the desired peptide.

The details of the method for producing each peptide and the evaluation of their antigenicity follow.

EXAMPLE 1

Polypetides P31 and P35 were produced by the method described below.

(1) Preparation of HBsAg Particles

Plasma containing high reversed passive hemagglutination titers of HBsAg (subtype adr) and positive for HBeAg were pooled. The plasma pool was centrifuged at 37,000×g for 16 hours, and Dane particle were pelleted down. Small HBsAg particles with a diameter of 22-nm in the supernatant were isolated by a succession of steps involving continuous-flow ultracentrifigation and rate zonal ultracentrifugation in KBr and surcrose.

(2) Polyacrylamide Gel Electrophoresis

Six-hundred milligrams of purified HBsAg particles dissolved in 90 ml of Tris-HCl buffer (0.01M, pH 8.0) containing 1% (wt/vol) SDS and 1% (vol/vol) 2-mercaptoethanol were incubated at 37° C. for 30 min, and broken into their constituent polypeptides. The solution containing HBsAg polypeptides was subjected to preparative SDS gel electrophoresis in a 90 mm×90 mm column in a Macro Page apparatus (Virchower Instruments Ltd., Letchworth, England) after the method of Maizel. The method of Maizel is well known in the art. The sample was loaded onto a stacking gel (3% acrylamide) standing on a preparative gel (9% acrylamide), and electricity at 50 V was applied at 2° C. Fractions were collected every 30 min, desalted in a Sephadex G-25 column, and then lyophylized.

Analytical electrophoresis was performed in SDS polyacrylamide slab gel in a Hoeffer apparatus (Hoeffer Scientific Instruments, San Francisco, Calif.) Bromphenol Blue was added to the sample as an indicator of the migrating front. An electric current of 15 mA was applied while the indicator stayed in the stacking gel (3% acrylamide), and increased to 30 mA after the migrating front reached the separating gel (10% acrylamide).

After electrophoresis the gel was stained for protein with Coomassie Brilliant Blue and for carbohydrate with periodic acid by the method of Zacharius et al.

Figure 2:
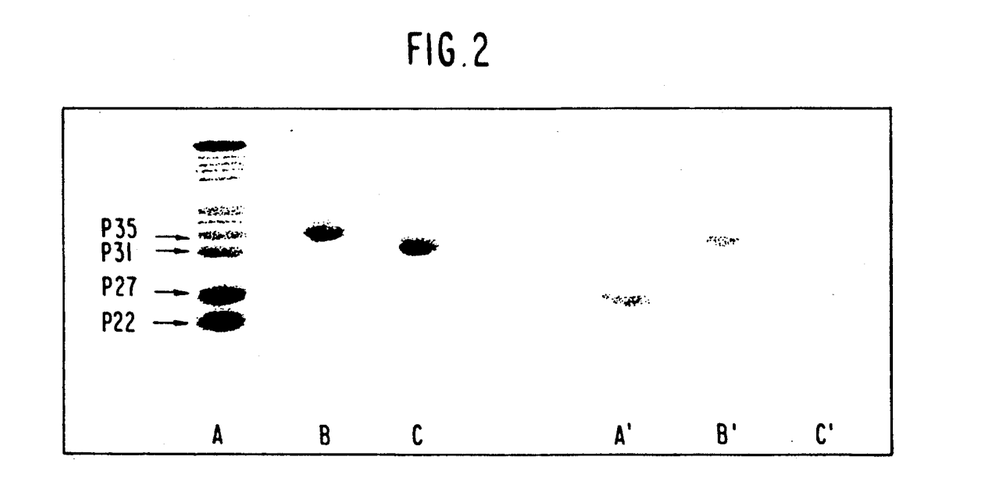
FIG. 2 is a distribution of protein segments on a polyacylamide gel.

The gel stained for protein was monitored for the absorbance at 550 nm by a Auto Scanner (Helena) for the tracing of polypeptide profile. Fractions of preparative SDS gel electrophoresis containing P31 and P35 were collected and they were purified. FIG. 2 shows sodium dodecyl sulfate polyacrylamide gel electrophoresis of HBsAg polypeptides. Hepatitis B surface antigen particles broken into constituent polypeptides (A) as well as P35 (B) and P31 (C) were run in analytical sodium dodecyl sulfate polyacrylamide gel electrophoresis and then stained for protein and for carbohydrates (A', B' and C'). Arrows indicate the positions of P35, P31, P27 and P22.

EXAMPLE 2

Asp-peptides and the polypeptide in which the 9th amino acid residue is replaced by leuine were obtained by the following methods. The C-terminus amino acid of the intended peptide was conjugated with polysytrene after the solid-phase method of Merrifield. Then, t-butoxycarbonyl amino acid was connected one after another toward the N-terminus, and a 19-amino acid peptide with a sequence of Asp-Pro-Arg-Val-Arg-Gly-Leu-Try-Phe-Pro-Ala-Gly-Ser-Ser-Ser-Gly-Thr-Val (Asp-peptide) was synthesized. The peptide in which the 9th amino acid of phenylalanine in the Asp-peptide was replaced by leucine was also synthesized. The obtained peptides were hydrolysed under a depressurized condition with 6N HCl at 110°C. for 24 hours, and the amino acid composition of the intended sequence was ascertained.

EXAMPLE 3

The immunogenicity of polypeptides P31 and P35 was confirmed for the eligibility of their use as hepatitis B vacines.

(1) The Receptor for Poly-HSA

Figure 3:
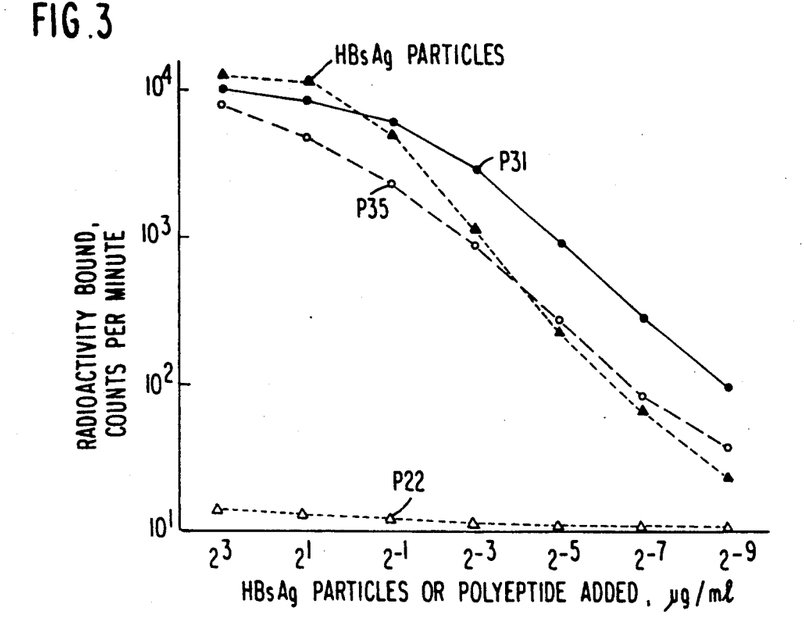
FIG. 3 is a plot of reactivity of HBsAg particles.
Figure 4:
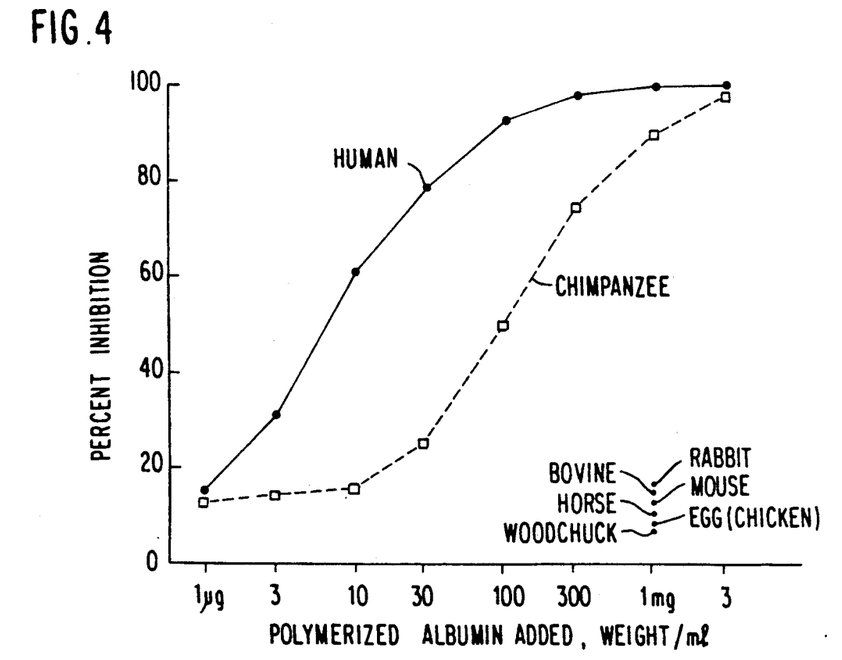
FIG. 4 is a plot of inhibition of polymerized albumin from various sources.

The reactivity of P31 and its glucosylated form, P35, with poly-HSA was evaluated along with HBsAg particles derived from HBeAg-positive plasma, P22 and its glycosylated form, P27, that served as controls; see FIG. 3. For this purpose, poly-HSA was coated onto wells of a polyvinyl microtiter plate. The sample to be tested for the reactivity with poly-HSA was incubated in the well. Then, the binding of the sample to wells was determined by the binding of radiolabeled antibody directed to the antigenic determinant(s) of HBsAg shared by all samples.

As is illustrated in FIG. 3, both P31 and P35 exhibited the reactivity with poly-HSA with a binding curve identical to that of HBsAg particles derived from the HBeAg-positive plasma. In sharp contrast, neither P22 nor P27 showed any appreciable binding with poly-HSA.

(2) Species Specificity

It is generally accepted that only humans and chimpanzees are vulnerable to the infection with HBV, while the other species of animals do not have the susceptibility to HBV.

Therefore, P31 was tested for the species-specificity. Albumin fractions from sera of various animals were polymerized with glutaraldehyde and coated onto wells of a polyvinyl microtiter plate. P31 was added to each well. The binding of P31 to wells was tested for by radiolabeled anti-HBs that was subsequently added to each well. Only polymerized albumins from humans and chimpanzees bound with P31; polymerized albumins from rabbit, cow, mouse, horse, egg and woodchuck did not reveal any appreciable binding with P31.

EXAMPLE 4

Immunogenicity of the Asp-peptide of the present patent claim was confirmed by the following method.

(1) Coupling with Chicken Egg Albumin (Ovalbumin)

The Asp-peptide was coupled with ovalbumin (Sigma Chemical Co., St. Louis, Mo.) that served as a carrier protein by means of 1-ethyl-3(3-dimethylaminopropyl) carboxydimide (Sigma Chemical Co., St. Louis, Mo.) Briefly, 5 mg of the synthetic peptide and 1.5 mg of ovalbumin were dissolved in 5 ml of physiological saline, allowed to stand at room temperature overnight, and then dyalysed against physiological saline for 2 days.

(2) Immunization

Each of female guinea pigs of Hartley strain received subcutaneously 0.1 ml of saline containing 1 mg of the synthetic peptide (conjugated with obalbumin) emulsified in 0.2 ml of Freund's complete adjuvant. Four weeks later, guinea pigs were boosted with the same inoculum. After an additional week, blood was obtained by cardiac puncture and the antiserum was obtained.

(3) Determination of Antibody by Radioimmunoassay

The activity of the obtained antisera was tested by a solid-phase sandwich-type radiommunoassay, as well as by the inhibition therof.

For the sandwich-type method, wells of a polyvinyl microtiter plate received 100 μl of buffer containing one or other of the following reagents at 100 μg/ml: polymerized human serum albumin, mouse monoclonal antibody against pre-S polypeptide, HBsAg particle preparation of subtype adr purified either from HBeAg-positive or anti-HBeAg-positive plasma, HBsAg particles of subtype adw derived from HBeAg-positive plasma, HBsAg particles of subtype adr isolated from HBeAg-positive plasma and then treated with pronase to deprive them of the poly-HSA receptor, P31, P22 and the synthetic peptide. The plate was incubated at room temperature for 1 hour and washed.

The test sample (50 μl) was transferred to wells, and the plate was incubated at 37°C. for 90 min. After the plate was washed, each well received 100 μl of buffer containing radiolabeled anti HBs or monoclonal anti-pre-S, or P31. The plate was incubated at 37°C. for 90 min and then washed. Wells were cut apart and the radioactivity of individual well was counted. Between each step of adding reagents, the plate was washed with saline for 5 times.

For the inhibition test, 50 μl of the test sample was mixed with 50 μl of monoclonal anti-pre-S labeled with $^{125}$I, and incubated at 37° C. for 90 min. A 50μl portion of the mixture was delivered to wells of a microtiter plate precoated with P31, and the plate was incubated at 37°C. for 90 min. In parallel, 50 μl of buffer were processed in the identical manner as the test sample. The result was expressed by percent inhibition, i.e., (cpm of the sample)/(cpm of buffer)×100. The radioiodination of γ-globulin was performed by the chloramine-T method at a specific activity of 5 μCi/ug after the method of Greenwood et al. (Biochemical J., 89:114–123, 1963).

(4) Monoclonal Antibodies

Female BALB/c mice received intraperitoneally, one or other of Asp-peptide, P31 and HBsAg particles treated with SDS and 2-mercaptoethanol, each emulsified in Freund's complete adjuvant. Mice were boosted 3 weeks later with the same inoculum. After additional 3 days, their spleen were taken out and immune spleen cells were harvested. Hybridization, cloning, and subsequent culture were performed by the method described by Oi and Herzenberg (Immunoglobulin producing hybrid cell lines. In Selected Methods in Cellular Immunology, Freeman and Co., San Francisco, pp 351–372, 1980).

Culture media were tested for the antibody against the pre-S polypeptide by the following 2 different methods. In the hemagglutination assay, SRBC were coated with HBsAg particles obtained from HBeAg-positive plasma, or the same lot of HBsAg but after the treatment with pronase that deprived them of the receptor for poly-HSA.

For another approach to the evaluation of the antibody specificity, wells of a microtiter plate were coated either with P31 or P22. Culture media were incubated in these wells. Subsequently, the bound immunoglobulin was detected by the rabbit anti-mouse γ-globulin labeled with radioiodine.

Clones secreting the desired antibodies were selected and propagated in the peritoneal cavity of mice that had been made ascitic by means of Pristane. Ascites fluid was harvested after 14 days of implantation, and γ-globulin fraction was precipitated with 1.33M ammonium sulfate and then purified by a column of Sephadex G-200 (Pharmacia Fine Chemicals, Piscataway, N.J.)

(5) Reactivity of Monoclonal Antibodies with Various HBsAg Peptides

Eight batches of monoclonal antibody of IgG class were tested for the inhibition of the binding of poly-HSA with HBsAg particles with the receptor in a solid-phase sandwich radioimmunoassay. See Table 2. All the monoclonals tested exhibited the inhibitory activity, thereby indicating the eligibility of Asp-peptide for use as a hepatitis B vaccine.

(6) Immunogenicity of Synthetic Peptide

In order to evaluate its immunogenicity, the synthetic peptide was conjugated with ovalbumin, and emulsified in Freund's complete adjuvant. The inoculum containing 1 mg of the peptide was given to each of 3 guinea pigs intracutaneously. They were boosted 4 weeks later with the same inoculum, and exanguinated after an additional week. The antisera obtained were tested for the antibody activity by the sandwich-type radioimmunoassay by the method described below.

Wells of a microtiter plate were coated with one or other of HBsAg particles of subtype adr or adw derived from HBeAg-positive plasma, the same lot of HBsAg/adr but after the incubation with pronase, HBsAg particles of subtype adr obtained from anti-HBe-positive plasma, P31 or P22. The test sample was delivered to wells, and after incubation and washing, they received P31 labeled with $^{125}$I. Thereafter, the radioactivity bound to individual well was counted.

Sera from the 3 guinea pigs that had been immunized with the synthetic peptide invariably bound with the peptide as shown in Table 3. In addition, they showed the binding activity with P31 (derived from HBsAg-/adr particles) and also with HBsAg particles of subtype adr and ayw isolated from HBeAg-positive plasma. These antisera, however, showed little, if any, binding activity with P22 or with HBsAg/adr particles obtained from HBeAg-positive plasma and then depried of P31 and P35 by a treatment with pronase. On the basis of these results, the Asp-peptide has the capacity of raising antibodies in guinea pigs that bind with HBsAg particles derived from HBeAg-positive plasma and rich in P31 and P35. Since these antibodies can bind equally with HBsAg particles of subtypes adr and ayw, they are directed to the eptiope commonly expressed by the pre-S amino acid sequence irrespective of subtypes of HBV.

TABLE 3

Immunogenicity of OVA conjugated peptide.

| Solid phase | guinea pig #1 | guinea pig #2 | guinea pig #3 | unprimed control |
|---|---|---|---|---|
| HBsAg | | | | |
| adr(eAg+) | 4,404 | 2,838 | 3,604 | 159 |
| adr | 227 | 156 | 243 | 154 |
| eAg + Pronase treated | | | | |
| adr(eAb+) | 637 | 370 | 481 | 134 |
| adw(eAg+) | 2,310 | 1,462 | 2,648 | 169 |
| Peptide | | | | |
| P31(adr) | 2,124 | 1,410 | 2,436 | 95 |
| P22(adr) | 366 | 322 | 454 | 85 |
| peptide | 742 | 472 | 998 | 74 |
| The 1st item of the claim for Patent | | | | |
| non solid phase | 116 | 115 | 134 | |
| | | | | (cpm) |

The peptide in which the 9th amino acid residue is replaced by leucine was tested in a similar method, and is immunogenicity was fully confirmed.

EXAMPLE 5

The reactivity of the pre-S peptide was tested as follows.

(1) Monoclonal body (Hyb-4408)

The specificity of the monoclonal antibody (Hyb-4408) directed to the pre-S region amino acid sequence of P31 is given in Table 4. This monoclonal showed a high reactivity with P31 but a low reactivity with P22, thereby attesting to its specificity to the pre-S region peptide.

TABLE 4

Specificity of the monoclonal antibody (No. 4408) against amino acid sequence coded by the Pre-S region of HBV-DNA(a)

| | Radiolabelled antibody (cpm) | | |
|---|---|---|---|
| Antigen fixed to wells | Anti-Pre-S (4408) | Control(b) | Δ cpm |
| P31 | 2184 | 70 | 2114 |
| P22 | 124 | 59 | 65 |
| HBsAg from HBeAg-positive plasma | 1418 | 52 | 1366 |
| HBsAg from anti-HBe antibody positive plasma | 71 | 57 | 14 |
| HBsAg from HBeAg positive plasma treated with | 81 | 63 | 18 |

TABLE 4-continued

Specificity of the monoclonal antibody (No. 4408) against amino acid sequence coded by the Pre-S region of HBV-DNA(a)

| | Radiolabelled antibody (cpm) | | |
|---|---|---|---|
| Antigen fixed to wells | Anti-Pre-S (4408) | Control(b) | Δ cpm |
| pronase(c) | | | |

(a)HBsAg of various categories, as well as HBsAg polypeptides (50 μg/ml) were coated onto wells of a microtiter plate and tested for the reactivity with radiolabelled monoclonal antibody against Pre-S amino acid sequence (anti-Pre-S No. 4408:1 × 10⁵ cpm).
(b)IgG fraction of normal mouse serum.
(c)HBsAg particles that lost the receptor for poly-HSA by the treatment with pronase.
HBV.DNA = Hepatitis B Virus.DeoxyriboNucleic Acid.
HBeAg = Hepatitis B e Antigen
HBsAg = Hepatitis B surface Antigen
IgG = Immunoglobulin G.

(2) Isolation of the Pre-S Peptide from P31

The protein component of P31 is deduced to be made of P22 and additional 55 amino acid residues on its N-terminus. Since there can be found no methionine residues between the N-terminus of P22 and that of P31, a method to split polypeptide at methionine by means of CNBr is expected to liberate the 55-amino acid pre-S peptide from P31. The conventional condition of the reaction in the presence of 70% formic acid and 0.1N HCl completely inactivated the receptor for poly-HSA. Therefore, the splitting with CNBr was carried out in a solution containing SDS. After the treatment, obtained peptides were separated by high-performance liquid chromatography. The fraction containing the presumed pre-S peptide were collected, and subjected to amino acid analysis. For the determination of amino acid composition of the obtained peptide, its content of alanine was estimated at 4 moles as on the pre-S nucleotide sequence of HBV-DNA, and the other amino acid residues were calculated pro rata. The results obtained was essentially same with the pre-S peptide of 55 amino acid residues that was deduced from the nucleotide sequence of pre-S region of HBV-DNA of subtype adr.

(3) Reactivity of Monoclonal Anti-Pre-S Antibody (Hyb-4408) and the Pre-S Peptide Derived from P31

The pre-S peptide isolated from P31 was tested for the reactivity with the monoclonal antibody (Hyb-4408) that had been raised against P31 and shown to be directed to its part encoded by the pre-S region and responsible for the receptor for poly-HSA. For this purpose, portions of buffer containing serial concentrations of pre-S peptide were incubated with a solution containing radiolabeled Hyb-4408 and incubated. An alliquot of this mixture was then transferred to wells of a microtiter plate coated with P31. The inhibition by the sample on the binding of radiolabeled Hyb-4408 with P31 was estimated using the value of similarly treated buffer as a reference as shown in Table 5. The inhibition on the binding of $^{125}$I-Hyb-4408 increased pari passu with increasing concentration of pre-S peptide, with a linearity over a range from 3 to 100 μg/ml. These results were taken as the clear evidence for the binding of pre-S peptide with the monoclonal anti-pre-S antibody (Hyb-4408).

TABLE 5

Reactivity of anti-Pre-S monoclonal antibody Hyb 4408 and Pre-S peptide.

| Quantity of Pre-S peptide | % inhibition (1) |
|---|---|
| 1 μg/ml | 15.2 |
| 3 | 25.5 |
| 10 | 41.3 |
| 30 | 65.7 |
| 100 | 91.8 |
| 0 (Saline) | 0 |

(1) Mixed the sample (50 μl) with $^{125}$I anti-Pre-S monoclonal antibody (50 μl) at 37° C., incubated for 90 minutes, and then 50 μl of the mixture was transferred to a microtiter plate well coated with P31 for inhibition reaction at 37° C., for 90 minutes.

(5) Binding of Poly-HSA with the Pre-S Peptide

The pre-S peptide was tested for the reactivity with poly-HSA in a sandwich-type radioimmunoassay. The solution containing pre-S peptide was added to wells of a microtiter plate pre-coated with poly-HSA. The binding of the pre-S peptide to poly-HSA was then evaluated by radiolabeled monoclonal anti-pre-S antibody subsequently added to wells. As is shown in Table 6, pre-S peptide bound with poly-HSA, thereby indicating that the receptor for poly-HSA is borne specifically by the pre-S peptide portion in P31.

TABLE 6

Evidence of Poly-HSA receptor on Pre-S peptide.

| Sample | Reactivity (a) |
|---|---|
| P31 (100 ng/ml) | 2958 cpm |
| Pre-S peptide (45 μg/ml) | 2444 |
| Bf | 105 |

(a) 50 μl of samples were poured into well coated with Poly-HSA. Radiolabelled anti-Pre-S monoclonal antibody (Hyb 4408) was used as 2nd antibody. Radioactivities of well were measured.

The vaccines of the present invention may take several different forms. Thus, they may be linked to a carrier such as a protein carrier tetnus toxoid, keyhole limpet hemocyanin, ovalbumin, or any other protein or polypeptide which would elicit a good T-cell response in the host. Non-protein carriers such as lipids, liposomes may also be used. Adjuvants may be used with the vaccines such as aluminum hydroxide (alum), muramyl dipeptide, any acceptable oil and water combination, any substance which stimulates T helper calls such as bacterial cell components—endotoxins, cell wall components, or chemicals that stimulate T helper cells. Such carriers, adjuvants and the like are known in the art. The peptide may also be polymerized or linked to itself to produce a high molecular weight molecules or render it immunogenic by glutaraldehyde cross-linking for example.

Further variations and modifications of the invention will be apparent to those skilled in the art which are intended to be encompassed by the claims appended hereto.

What is claimed is:

1. A polypeptide having the amino acid sequence of Asp-Pro-Arg-Val-Arg-Gly-Leu-Try-Phe-Pro-Ala-Gly-Gly-Ser-Ser-Ser-Gly-Thr-Val.

2. A polypeptide having the amino acid sequence of Asp-Pro-Arg-Val-Arg-Gly-Leu-Try-Leu-Pro-Ala-Gly-Gly-Ser-Ser-Ser-Gly-Thr-Val.

3. A composition for immunizing humans or chimpanzees against Hepatitis B virus infection, said composition having a polypeptide or polypeptide fragment as defined in claim 1 and a pharmaceutically acceptable carrier.

4. A composition for immunizing humans or chimpanzees against Hepatitis B virus infection, said composition having a polypeptide or polypeptide fragment as defined in claim 2 and a pharmaceutically acceptable carrier.

5. A method for immunizing against or reducing the incidence and effects of Hepatitis B virus infection in humans or chimpanzees by administration thereto a pharmaceutical composition having an effective amount of a polypeptide of claim 1.

6. A method for immunizing against or reducing the incidence and effects of Hepatitis B virus infection in humans or chimpanzees by administration thereto a pharmaceutical composition having an effective amount of polypeptide of claim 2.

7. A method of inhibiting hepatitis B virus infection comprising administering a polypeptide vaccine according to claim 1.

8. A method of inhibiting hepatitis B virus infection comprising administering a polypeptide vaccine according to claim 2.

* * * * *